(12) United States Patent
Myers et al.

(10) Patent No.: US 10,679,482 B2
(45) Date of Patent: *Jun. 9, 2020

(54) WEARABLE ALERT SYSTEM

(71) Applicant: Locator IP, L.P., State College, PA (US)

(72) Inventors: Joel N. Myers, State College, PA (US); Lachlan Myers, State College, PA (US); Michael R. Root, Edmond, OK (US); Michael R. Smith, Wichita, KS (US)

(73) Assignee: Locator IP, L.P., State College, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/533,044

(22) Filed: Aug. 6, 2019

(65) Prior Publication Data

US 2019/0362612 A1 Nov. 28, 2019

Related U.S. Application Data

(63) Continuation of application No. 16/067,381, filed as application No. PCT/US2017/012155 on Jan. 4, 2017, now Pat. No. 10,417,893.

(Continued)

(51) Int. Cl.
*A61B 5/00* (2006.01)
*G08B 21/04* (2006.01)
(Continued)

(52) U.S. Cl.
CPC ........ *G08B 21/0446* (2013.01); *A61B 5/0004* (2013.01); *A61B 5/0022* (2013.01);
(Continued)

(58) Field of Classification Search
CPC .............. G08B 21/0446; G08B 27/005; G08B 25/016; A61B 5/0004; A61B 5/0022; A61B 5/6804; A61B 5/747

See application file for complete search history.

(56) References Cited

U.S. PATENT DOCUMENTS 6,028,514 A 2/2000 Lemelson
7,337,146 B2 2/2008 Heelan et al.
(Continued)

FOREIGN PATENT DOCUMENTS

JP 2009193315 A 8/2009
JP 2012522561 A 9/2012
(Continued)

OTHER PUBLICATIONS

English abstract; Russian Application No. RU113394; Publication Date: Feb. 10, 2012; 2 pages.
(Continued)

*Primary Examiner* — Munear T Akki
(74) *Attorney, Agent, or Firm* — Blank Rome LLP (57) ABSTRACT

A system that stores a user profile that associates a wearable alert device with a user and includes contact information for an emergency contact, receives information indicative of a real-time location of the wearable alert device and information indicating that the user of the wearable alert device is potentially experiencing an abnormal physiological condition, and outputs an alert for transmittal to the emergency contact that includes an indication that the user is potentially experiencing the abnormal physiological condition and the real-time location of the wearable alert device.

18 Claims, 3 Drawing Sheets

Related U.S. Application Data (60) Provisional application No. 62/337,648, filed on May 17, 2016, provisional application No. 62/298,794, filed on Feb. 23, 2016, provisional application No. 62/274,685, filed on Jan. 4, 2016.

(51) Int. Cl.
  *G08B 27/00* (2006.01)
  *G08B 25/01* (2006.01)

(52) U.S. Cl.
  CPC ............ *A61B 5/6804* (2013.01); *A61B 5/747* (2013.01); *G08B 27/005* (2013.01); *G08B 25/016* (2013.01)

(56) References Cited

U.S. PATENT DOCUMENTS

| | | | |
|---|---|---|---|
| 8,611,927 B2 | 12/2013 | Root et al. | |
| 9,375,143 B2 | 6/2016 | Matsuno et al. | |
| 2002/0116080 A1* | 8/2002 | Birnbach | A61B 5/0002 700/66 |
| 2004/0006694 A1 | 1/2004 | Heelan | |
| 2009/0171170 A1* | 7/2009 | Li | A61B 5/00 600/301 |
| 2010/0231379 A1* | 9/2010 | Hutzler | A61B 5/411 340/539.12 |
| 2014/0276238 A1* | 9/2014 | Osorio | A61B 5/0205 600/595 |
| 2015/0094544 A1* | 4/2015 | Spolin | A61B 5/7275 600/301 |
| 2015/0161876 A1 | 6/2015 | Castillo | |
| 2015/0182843 A1 | 7/2015 | Esposito | |
| 2015/0332581 A1* | 11/2015 | Gaurav | G08B 25/016 340/539.13 |
| 2016/0038055 A1* | 2/2016 | Wheeler | A61B 5/0533 600/547 |

FOREIGN PATENT DOCUMENTS

| | | |
|---|---|---|
| JP | 2014213071 A | 11/2014 |
| RU | 113394 U1 | 2/2012 |
| WO | 2010113092 A1 | 10/2010 |

OTHER PUBLICATIONS

Won-Jae Yi et al., "Wearable sensor data fusion for remote health assessment and fall detection", IEEE International Conference on Electro/Information Technology, pp. 303-307, https://ieeexplore.ieee.org/document/6871782; 5 pages.

English translation of Japanese Publication No. JP2009193315; Publication Date: Aug. 27, 2009; 50 pages.

English translation of Japanese Publication No. JP2012522561; Publication Date: Sep. 27, 2012; 11 pages.

English translation of Japanese Publication No. JP2014213071; Publication Date: Nov. 17, 2014; 32 pages.

Maged N. Kamel Boulos et al., "Real-time locating systems (RTLS) in healthcare: a condensed primer", International Journal of Health Geographics, Biomed Cental Ltd, London, GB, vol. 11, No. 1, Jun. 28, 2012 (Jun. 28, 2012), p. 25, XP021133018, ISSN: 1476-072X, DOI: 1186/1476-072X-11-25.

\* cited by examiner

WEARABLE ALERT SYSTEM

CROSS REFERENCE TO RELATED APPLICATIONS

This application is a continuation of co-pending U.S. patent application Ser. No. 16/067,381, filed Jun. 29, 2018, which is a national stage application of PCT Pat. Appl. No. PCT/US2017/012155, filed Jan. 4, 2017, which claims priority to U.S. Prov. Pat. Appl. No. 62/337,648, filed May 17, 2016, U.S. Prov. Pat. Appl. No. 62/298,794, filed Feb. 23, 2016, and U.S. Prov. Pat. Appl. No. 62/274,685, filed Jan. 4, 2016, the entire contents of which are hereby incorporated by reference. This application is also related to U.S. patent application Ser. No. 14/979,434, filed Dec. 27, 2015, U.S. Prov. Pat. Appl. No. 62/096,631, filed Dec. 24, 2014, U.S. Pat. No. 8,229,467, filed Jan. 19, 2006, and U.S. Pat. No. 8,611,927, filed Mar. 31, 2011, the entire contents of which are hereby incorporated by reference.

BACKGROUND

Handheld multi-functional devices such as smartphones provide countless benefits. Handheld multifunction devices, however, have a number of drawbacks. Increases in functionality and processing power (and decreases in size and weight) all reduce battery life. Meanwhile, devices that are stored in pockets and purses cannot continuously monitor users via sensors or, in most instances, immediately or consistently alert users (e.g., via tactile feedback). Furthermore, handheld multifunction devices are expensive to manufacture and purchase, causing some users to use older models with older functionality or features instead of frequently replacing their device each time a new version is released.

Compared to handheld multifunction devices, devices that are wearable on a user's clothing or body are less cumbersome to carry, easier to interact with, provide fewer opportunities for damage or loss or theft, can continuously monitor users via sensors, and can immediately and consistently alert a user (e.g., via tactile feedback). Meanwhile, wearable devices that provide fewer features can be manufactured at a lower cost than handheld multifunction devices, making it easier for users to purchase a new device or replace an existing device. Finally, wearable devices that provide fewer features may have a longer battery life than handheld multifunction devices, particularly wearable devices that include energy harvesting devices that capture and store energy (e.g., from light, wind, deformation, and/or kinetic energy of the user). Devices that are small enough and/or flexible enough to be implanted on a user's body are even easier to carry and interact with than devices that are wearable on the user's clothing or body. Additionally, implantable devices may be even less prone to damage or loss or theft.

A wearable device (that is wearable or implantable on a user's clothing or body) can be used to automatically and/or continuously monitor the real-time (or near real-time) location of the user. Meanwhile, cloud-based software applications have the potential to access, process, and output a growing array of real-time data and predictive data about conditions at different locations, including information and predictions regarding potentially dangerous conditions (e.g., weather conditions, public safety conditions, and/or environmental conditions). Accordingly, there is a need for a system that outputs an alert to a user in response to a determination that a wearable device is in the location of a geographic area of a potentially dangerous condition.

Additionally, given the ease of use of a wearable device and the ability to continuously monitor the physiological conditions of a user via a physiological sensor, there is a need for a system that pairs a wearable device that includes a physiological sensor with a remotely-stored user profile that includes the contact information of an emergency contact and outputs an alert for transmittal to the emergency contact that includes an indication that the user is potentially experiencing an abnormal physiological condition and the real-time location of the wearable alert device.

SUMMARY

In order to overcome those and other drawbacks in the prior art, a system is provided that stores a user profile that associates a wearable alert device with a user and includes contact information for an emergency contact, receives information indicative of a real-time location of the wearable alert device and information indicating that the user of the wearable alert device is potentially experiencing an abnormal physiological condition, and outputs an alert for transmittal to the emergency contact that includes an indication that the user is potentially experiencing an abnormal physiological condition and the real-time location of the wearable alert device.

BRIEF DESCRIPTION OF THE DRAWINGS

Aspects of exemplary embodiments may be better understood with reference to the accompanying drawings. The components in the drawings are not necessarily to scale, emphasis instead being placed upon illustrating the principles of exemplary embodiments.

DETAILED DESCRIPTION

Reference to the drawings illustrating various views of exemplary embodiments of the present invention is now made. In the drawings and the description of the drawings herein, certain terminology is used for convenience only and is not to be taken as limiting the embodiments of the present invention. Furthermore, in the drawings and the description below, like numerals indicate like elements throughout.

Figure 1:
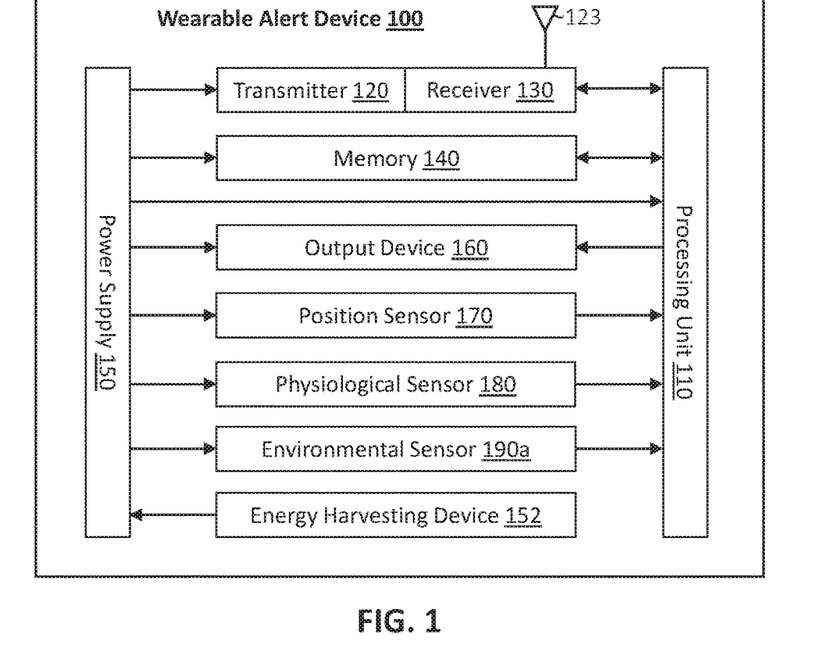
FIG. 1 is a block diagram of a wearable alert device according to an exemplary embodiment of the present invention.

FIG. 1 is a block diagram of a wearable alert device 100 according to an exemplary embodiment of the present invention. The wearable alert device 100 includes a processing unit 110, a transmitter 120, a receiver 130, one or more antennas 123, memory 140, a power supply 150, and an output device 160. The wearable alert device 100 may also include an energy harvesting device 152, one or more position sensors 170, one or more physiological sensors 180, and/or one or more environmental sensors 190a.

The wearable alert device 100 may be incorporated into a piece of clothing such as a shoe, pants, a shirt, a jacket, a wristband, a watch, glasses, a hat, etc. Alternatively, the wearable alert device 100 may be wearable on the body of a user. For example, the wearable alert device 100 may be wearable on the ear (similar to a Bluetooth headset), wearable in the ear (similar to a hearing aid), and wearable over the eyes (similar to virtual reality goggles or eyeglasses). In another example, the wearable alert device 100 may include thin-film electronics laminated to the skin, near-permanent electric paint, temporary flexible appliqués, etc. Alternatively, the wearable alert device 100 may be implantable in the body of the user. For example, the wearable alert device 100 may be a nano- or micro-device implanted into bone marrow, placed in the subcutaneous tissue, sutured to the skull and hidden by hair, sutured on bone on top of the skin, or swallowed and used temporarily as the device passes through the digestive track.

The processing unit 110 may be any suitable device that carries out the instructions of a computer program by performing the arithmetic, logical, control and input/output (I/O) operations specified by the instructions. The processing unit 110 may include a central processing unit (CPU), a graphics processing unit (GPU), etc. The processing unit 110 may be realized as a single semiconductor chip or more than one chip.

The transmitter 120 may be any suitable device that wirelessly transmits information by generating a radio frequency signal and applying that signal to an antenna 123. The receiver 130 may be any suitable device that receives radio waves from an antenna 123 and converts information carried by the radio waves into a useable form. The transmitter 120 and the receiver 130 may be realized separately or may combined such that they share common circuitry and/or a single housing. The transmitter 120 and the receiver 130 may communicate with a cell network using any wireless communication standard such as the global system for mobile communications (GSM) standard, a code division multiple access (CDMA) standard, a long term evolution (LTE) standard, worldwide interoperability for microwave access (WiMAX), etc. Additionally or alternatively, the transmitter 120 and the receiver 130 may communicate with another portable electronic device (e.g., a smartphone, a vehicle, etc.) using any wireless communication standard such as Bluetooth, an 802.11 standard, etc.

The memory 140 may be any suitable device that stores instructions that, when executed by the processing unit 110, cause the wearable alert device 100 to perform the functions described herein. The memory 140 may include a non-transitory computer readable storage medium, such as a hard disk, solid-state memory, etc.

The power supply 150 may be any suitable device that supplies energy to the hardware elements of the wearable alert device 100 such as the processing unit 110, the transmitter 120, the receiver 130, the memory 140, etc. The power supply 150 may include, for example, a battery. The power supply 150 may include an energy harvesting device 152. The energy harvesting device 152 may be any suitable device that captures energy from external sources for storage in the power supply 150. The energy harvesting device 152 may include, for example, photovoltaic cells that capture solar energy and/or energy from ambient light, a micro wind turbine that captures wind energy, piezoelectric crystals or fibers (located, for example, in the heel of a shoe) that generate an electric voltage when deformed, a kinetic energy harvester that captures kinetic energy (for example, via movement of a magnet in an electromagnetic generator) as the wearable alert device 100 is in motion, etc.

The output device 160 may be any suitable device that outputs an alert to a user. The alert may be visual, audible, haptic, etc. The output device 160 may include a light, such as a light emitting diode (LED) that outputs a visual alert to the user. Additionally or alternatively, the output device 160 may include a display (e.g., a liquid crystal display (LCD), a light emitting polymer display (LPD), an LED display, an organic light emitting diode (OLED) display, etc.). The output device 160 may include a speaker that outputs an audible alert to the user. The output device 160 may include an oscillator or other device that provides a haptic or tactile alert to the user.

The position sensors 170 may include any suitable device that determines the real-time or near real-time location, velocity, acceleration, and/or orientation of the wearable alert device 100. The position sensors 170 may include, for example, a global positioning system (GPS) receiver, an altimeter, an accelerometer, a gyrometer, a magnetometer, a compass, an inclinometer, a device orientation sensor, etc. The position sensors 170 may also include one or more sensors to determine motion of the ground, such as a seismometer.

The physiological sensors 180 may include any suitable device that determines at least one physiological parameter of a user. A physiological sensor 180 may determine, for example, body temperature, heart rate, brain activity, muscle motion, sweat rate, blood pressure, pulse oximetry, blood chemistry (e.g., insulin levels, blood-alcohol content, etc.), respiratory rate, brain waves, one or more properties of the human nervous system (e.g., passive and/or active electrodermal activity), etc.

The environmental sensors 190a may include any suitable device that detects an abnormal or potentially dangerous environmental condition. An environmental sensor 190a may include, for example, a pollen sensor that measures pollen count, a particulate matter sensor that measures particulate matter concentration, a gas sensor that detects the presence of noxious gasses and/or measures concentrations of greenhouse gas, a solar radiation sensor (e.g., a pyranometer, a net radiometer, a quantum sensor, a pyrheliometer, etc.) a radiation sensor (e.g., a Geiger counter), etc. The output device 160 may output an alert in response to a determination by the environmental sensor 190a of an abnormal or potentially dangerous environmental condition. Additionally, as described in more detail below, the wearable alert device 100 may output information indicative of the potentially dangerous environmental condition to the wearable alert system 300 such that the wearable alert system 300 may output an alert to other users in the vicinity.

Figure 2:
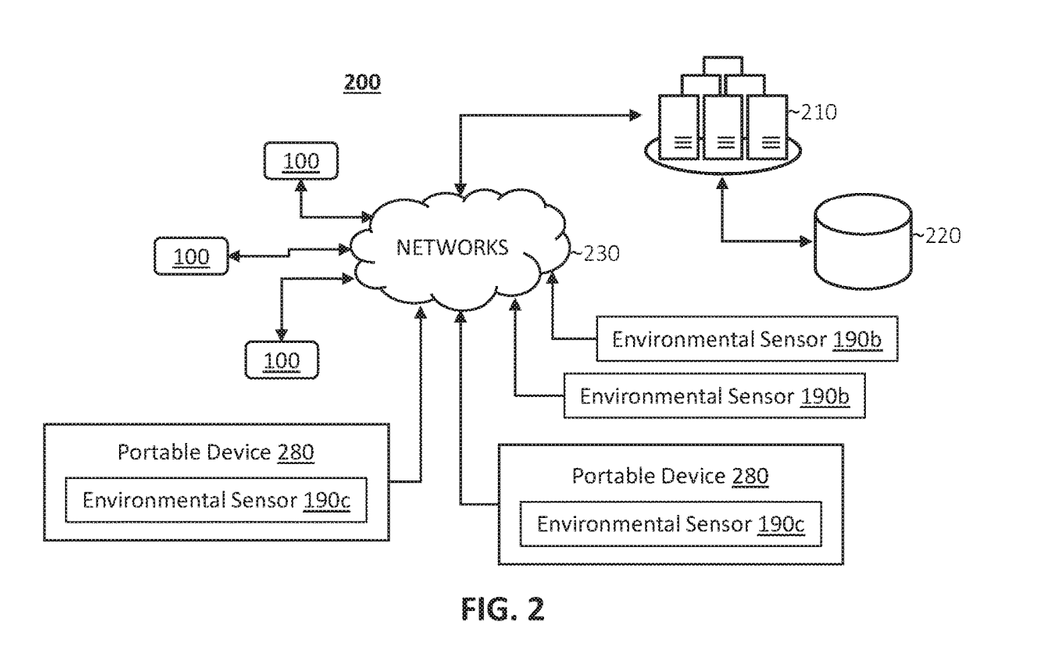
FIG. 2 is a drawing illustrating the architecture of a wearable alert system according to an exemplary embodiment of the present invention.

FIG. 2 is a drawing illustrating the architecture 200 of the wearable alert system according to an exemplary embodiment of the present invention. The architecture 200 includes one or more servers 210 and one or more storage devices 220 connected to a plurality of wearable alert devices 100 via one or more communications networks 230. The wearable alert devices 100 may include environmental sensors 190a as described above. Additionally or alternatively, the architecture 200 may include stationary environmental sensors 190b and/or environmental sensors 190c incorporated within portable devices 280.

The one or more servers 210 may be any suitable computing device that executes instructions such that the wearable alert system performs the functions described herein. The one or more servers 210 may include internal storage and a processing unit. The one or more storage devices 220 may include a non-transitory computer readable storage medium, such as a hard disk, solid-state memory, etc. The networks 230 may include any combination of the internet, cellular networks, wide area networks (WAN), local area networks (LAN), etc. Communication via the networks 230 may be realized by wired and/or wireless connections.

Similar to the environmental sensors 190a described above, the stationary environmental sensors 190b and the environmental sensors 190c incorporated within portable devices 280 may include any suitable device that detects an abnormal or potentially dangerous environmental condition. The stationary environmental sensors 190b may be free standing sensors such as the sensors maintained by the U.S. Environmental Protection Agency. The portable devices 280 may be cellular phones, communications devices for first responders, soldiers, etc. Similar to the wearable alert device 100, a portable device 280 may include one or more position sensors to determine the real-time location of the portable environmental sensor 190.

The wearable alert devices 100 may directly communicate with one or more networks 230 or may communicate with another portable electronic device (e.g., a smartphone, a vehicle, etc.) that may communicate with one or more networks 230.

Figure 3:
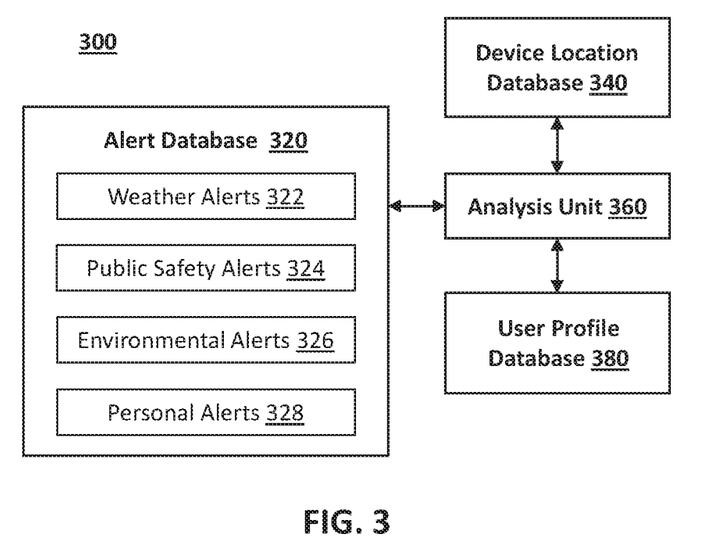
FIG. 3 is a block diagram of the wearable alert system according to an exemplary embodiment of the present invention.

FIG. 3 is a block diagram of the wearable alert system 300 according to an exemplary embodiment of the present invention. The wearable alert system 300 includes an alert database 320, a device location database 340, and an analysis unit 360. The wearable alert system 300 may also include a user profile database 380.

The alert database 320 stores information regarding potentially dangerous conditions in geographic areas, including weather alerts 322, public safety alerts 324, and/or environmental alerts 326. The alert database 320 may be any organized collection of information, whether stored on a single tangible device or multiple tangible devices. The alert database 320 may be stored, for example, in one or more of the storage devices 220.

The weather alerts 322 may include weather warnings (indicating the presence of a potentially dangerous weather pattern in a geographic area) and weather watches (indicating that conditions are favorable in a geographic area for the development of a potentially dangerous weather pattern). The weather alerts 322 may include, for example, river flood warnings, thunderstorm watch boxes, tornado watch boxes, mesoscale discussions, polygon warnings, zone/country warnings, outlooks, advisories, watches, special weather statements, lightning warnings, thunderstorm warnings, heavy rain warnings, high wind warnings, high or low temperature warnings, local storm reports, and/or hurricane impact forecasts. The weather alerts 322 may also include information indicative of radically changing forecasts, firsthand observations of weather conditions, etc. The weather alerts 322 may be received, for example, from AccuWeather, Inc., AccuWeather Enterprise Solutions, Inc., governmental agencies (such as the National Weather Service (NWS), the National Hurricane Center (NHC), Environment Canada, the U.K. Meteorologic Service, the Japan Meteorological Agency, etc.), other private companies (such as Vaisalia's U.S. National Lightning Detection Network, Weather Decision Technologies, Inc.), individuals (such as members of the Spotter Network), etc. A weather alert 322 may include information indicative of the severity of the potentially dangerous weather pattern. The severity of the potentially dangerous weather pattern may be determined based on the likelihood that the potentially dangerous weather pattern will cause bodily harm and/or the severity of bodily harm that the potentially dangerous weather pattern may cause.

The public safety alerts 324 may be information indicative of a potentially dangerous public safety conditions. The public safety alerts 324 may be received from law enforcement agencies, fire departments, and/or other first responders, government agencies (e.g., federal, state, county, city, etc.) such as armed forces agencies (e.g., Army, National Guard, Coast Guard, etc.) and civil defense agencies (e.g., the Department of Homeland Security), public or private utility companies (for example, an alert of a power outage in a geographic area), etc. A public safety alert 324 may include information indicative of the severity of the potentially dangerous public safety condition. The severity of the potentially dangerous public safety condition may be determined based on the likelihood that the potentially dangerous public safety condition will cause bodily harm and/or the severity of bodily harm that the potentially dangerous public safety condition may cause.

The environmental alerts 326 may be information indicative of a potentially dangerous environmental condition. Potentially dangerous environmental conditions may include radiation, poor air quality (e.g., noxious gasses, high particulate matter concentrations, high levels of greenhouse gasses such as carbon monoxide, carbon dioxide, ozone, methane, etc.), higher than normal solar radiation, high pollen count, etc. The severity of a potentially dangerous environmental condition may be determined based on the likelihood that the potentially dangerous environmental condition will cause bodily harm and/or the severity of bodily harm that the potentially environmental condition may cause. The wearable alert system 300 may determine the location of a potentially dangerous environmental condition based on the location of one or more environmental sensors 180 that detect the potentially dangerous environmental condition. For example, a wearable alert device 100 that includes an environmental sensor 180 may detect a potentially dangerous environmental condition and output information indicative of the potentially dangerous environmental condition to the wearable alert system 300. The wearable alert device 100 may output information indicative of the location of the wearable alert device 100. Alternatively, the wearable alert system 300 may determine the location of the wearable alert device 100.

In addition to generally applicable alerts regarding dangerous conditions in geographic areas (as described above), the alert database 320 may also store personal alerts 328 intended for specific users of the wearable alert system 300. The personal alerts 328 may be received from third parties. For example, a personal alert 328 may be received from a vehicle tracking system such as LoJack®, a subscription-based vehicle-based alert system such as OnStar®, a home security monitoring system, etc. (LOJACK is a registered trademark of Lojack Corporation. ONSTAR is a registered trademark of Onstar LLC.) A personal alert 328 (for example, an alert from a home security monitoring system) may be received from a third party system and output to a wearable alert device 100 regardless of the location of the wearable alert device 100. Additionally or alternatively, a personal alert 328 may be generated by the wearable alert system 300 or a third party system based on the location of a wearable alert device 100 associated with a user.

The device location database 340 stores information indicative of the real-time locations of the wearable alert devices 100. (As used herein, a "real-time" location of a wearable alert device 100 may include a near real-time location of the wearable alert device 100.) The device location database 340 may also store information indicative of the location of stationary environmental sensors 190 and/or the portable devices 280. The device location database 340 may be automatically and/or repeatedly updated to include information indicative of the real-time (or near real-time) dynamic location of the wearable alert devices 100 and/or the portable devices 280. The device location database 340 may be any organized collection of information, whether stored on a single tangible device or multiple tangible devices. The device location database 340 may be stored, for example, in one or more of the storage devices 220.

The location of a wearable alert device 100 and/or portable device 280 may be determined by the wearable alert device 100 and/or the portable device 280, for example, by one of the position sensors 170, cell network triangulation, network or cell tower identification, etc. Additionally or alternatively, the location of a wearable alert device 100 and/or portable device 280 may be determined by the server 210 or other network device, for example, by cell network triangulation, network or cell tower identification, etc. Additionally or alternatively, a wearable alert device 100 may pair with another portable electronic device (e.g., a smartphone, a vehicle, etc.) as described above and the wearable alert system 300 may determine the location of the wearable alert device 100 based on the location of the portable electronic device. The location of the portable electronic device may be determined by the portable electronic device (e.g., by GPS, cell network triangulation, network or cell tower identification, etc.) or by the server 210 or other network device (e.g., by cell network triangulation, network or cell tower identification, etc.).

The user profile database 380 stores a user profile for each user of the wearable alert system 300. The user profile database 380 may be any organized collection of information, whether stored on a single tangible device or multiple tangible devices. The user profile database 380 may be stored, for example, in one or more of the storage devices 220.

Each user profile may include information identifying one or more wearable alert devices 100. Additionally, each user profile may include user preferences indicating the types of alerts the user would like to receive. For example, a user profile may indicate a preference to receive weather alerts 322 and/or public safety alerts 324. In another example, a user profile may indicate a preference to receive weather alerts 322 and/or public safety alerts 324 that have specified severity. Additionally, each user profile may include information identifying third party services (e.g., a vehicle tracking system, a subscription-based vehicle-based alert system, a home security monitoring system, etc.) such that the user may receive personal alerts 328 via the wearable alert system 300. The user preferences may be received from each user. For example, the wearable alert system 300 may provide a user interface whereby a user is able to specify user preferences using a web browser, mobile phone application, etc.

The wearable alert system 300 may receive an alert regarding a potentially dangerous condition (e.g., a weather alert 322, public safety alert 324, an environmental alert 326, etc.) in a geographic area and output an alert to the wearable alert devices 100 in the geographic area (or the wearable alert devices 100 of users with a user profile indicating a preference to receive alerts regarding the potentially dangerous condition). Additionally or alternatively, the wearable alert system 300 may receive a personal alert for a user and output the personal alert to the wearable alert device 100 associated with the user.

As described above, the wearable alert system 300 may receive a personal alert 328 from a third party service intended for transmittal to the user regardless of a location of the wearable alert device 100 of the user. Additionally or alternatively, the wearable alert system 300 may also output personal alerts 328 generated based on the location of the user's wearable alert device 100.

The personal alerts 328 may be generated by the wearable alert system 300 or by a third party system. For example, the crime forecasting system described in U.S. patent application Ser. No. 14/979,434 generates "crime forecasts" by adjusting historical crime rates based on correlations between crime data and weather conditions. In that example, the wearable alert system 300 may output information indicative of the real-time location of a user's wearable alert device 100 to the crime forecasting system, which may generate a crime forecast based on the location of a user's wearable alert device 100, and the wearable alert system 300 may output an alert to the user's wearable alert device 100 if the crime forecast generated by the crime forecasting system exceeds a predetermined threshold (determined by the crime forecast system, specified in the user profile associated with the user, etc.).

In another example, the advisory system 8c described in U.S. Pat. No. 8,229,467 (e.g., a location-based dating system) includes an analysis unit 12c that matches real-time locations of locator and locatee communicator devices and matches user profile criteria associated with locators and locatees. In that example, the wearable alert system 300 may output information indicative of the real-time location of a user's wearable alert device 100 to the analysis unit 12c and output an alert to the user's wearable alert device 100 if the analysis unit 12c determines that a locatee with matching user profile criteria is within a predetermined spatial range (determined by the advisory system 8c, specified in the user profile associated with the user, etc.) of the user's wearable alert device 100.

In another example, the advisory system 8c described in U.S. Pat. No. 8,611,927 includes an analysis unit 12c that outputs an alert to a locator communicator device (e.g., a parent communicator device) when a locatee communicator device (e.g., a child communicator device) is outside a specified spatial range of the locator communicator device. In that example, the wearable alert system 300 may output information indicative of the real-time location of a user's wearable alert device 100 to the analysis unit 12c and output an alert to the user's wearable alert device 100 if the analysis unit 12c determines that a locatee communicator device is outside a specified spatial range (determined by the advisory system 8c, specified in the user profile associated with the user, etc.) of the user's wearable alert device 100. The advisory system 8c described in U.S. Pat. No. 8,611,927 may also output an alert to a locator communicator device if a locatee communicator device deviates from an expected travel path, does not arrive at a location by a specified time of arrival, arrives at a location by a specified time of arrival, is present at a specified geo-referenced area, etc. The wearable alert system 300 may output an alert to the user's wearable alert device 100 based on any determination by the advisory system 8c as described in U.S. Pat. No. 8,611,927.

Additionally or alternatively, the wearable alert system 300 may provide functionality for a user to forward an alert received via a wearable alert device 100 to another individual. For example, a bike rider on a 20-mile trip that receives a weather alert 322 regarding a potentially dangerous condition such as lightning may want to notify a friend or family member of a route change. In another example, a jogger that receives a public safety alert 324 may want to notify a friend or family member that the jogger is going to a safe place. In another example, a dog walker that receives a personal alert 328 from a home security monitoring system may want to notify the homeowner (if, for example, the homeowner is able to arrive at the house sooner or the dog walker is uncomfortable checking the house alone).

The wearable alert system 300 may provide functionality for a user to forward an alert (together with additional information) to another wearable alert device 100 or any other communication device (e.g., cell phone, computer, etc.) via email, text message, etc. The wearable alert device 100 may output the alert (and the additional information, if applicable) to the one or more communications networks 230 for transmittal to another wearable alert device 100 or other communication device. As described above, the wearable alert devices 100 may communicate with the one or more networks 230 directly or may communicate with another portable electronic device (e.g., a smartphone, a vehicle, etc.) that may communicate with the one or more networks 230. The wearable alert device 100 may include an input device (e.g., buttons, a touchscreen, etc.) enabling a user to enter the contact information of another individual (e.g., a telephone number, an email address, etc.) and any additional information that the user wishes to send along with the alert. Additionally or alternatively, the wearable alert system 300 may provide functionality for a user to store the contact information of one or more individuals in the user profile associated with the user and the wearable alert device 100 (for example, using a web browser, mobile phone application, etc.). In that example, the wearable alert device 100 may include a user input device that enables a user to select one or more individuals from the user profile (and input additional information to be sent along with the alert, if necessary). Additionally or alternatively, the wearable alert system 300 may provide functionality for a user to select one or more individuals from the user profile (and input additional information to be sent along with the alert, if necessary) using another communicator device (e.g., a mobile phone, a computer, etc.) via a web browser, mobile phone application, etc.

Additionally or alternatively, the wearable alert system 300 may be configured such that a wearable alert device 100 automatically outputs an alert to an emergency contact in response to a determination that the user is experiencing an abnormal physiological condition. As described above, the wearable alert device 100 may include one or more physiological sensors 180 that monitor, for example, body temperature, heart rate, brain activity, muscle motion, sweat rate, blood pressure, pulse oximetry, respiratory rate, etc. The wearable alert system 300 may determine that the user is experiencing an abnormal physiological condition based on a determination that one or more of the physiological sensors 180 is detecting a physiological parameter that is outside of normal range. Additionally or alternatively, the wearable alert system 300 may determine that the user is experiencing an abnormal physiological condition if the output from one or more position sensors 170 is consistent with a user falling to the ground.

Whether the user is potentially experiencing an abnormal physiological condition may be determined by the wearable alert device 100 and/or the analysis unit 360. In one embodiment, the wearable alert device 100 may be configured to determine whether the user of the wearable alert device 100 is potentially experiencing an abnormal physiological condition based on the physiological parameters (determined, for example, by the one or more physiological sensors 180) and/or the position of the user relative to the ground (determined, for example, by the one or more position sensors 170). In that embodiment, the wearable alert device 100 outputs an indication that the user is potentially experiencing the abnormal physiological condition to the communication network(s) 230 for transmittal to the analysis unit 360, which outputs an alert to the communication network(s) 230 for transmittal to the emergency contact. In another embodiment, the wearable alert device 100 may be configured to output information indicative of the physiological parameters (determined, for example, by the one or more physiological sensors 180) and/or information indicative of the position of the user relative to the ground (determined, for example, by the one or more position sensors 170) to the communication network(s) 230 for transmittal to the analysis unit 360. (The wearable alert device 100 may be configured to output the physiological and/or position information regularly or irregularly, on a fixed schedule, repeatedly, continuously, when the physiological and/or position information meets or exceeds a predetermined threshold, etc.) In that embodiment, the analysis unit 230 receives the physiological and/or position information, determines whether a user is potentially experiencing an abnormal physiological condition, and, if so, outputs an alert to the communication network(s) 230 for transmittal to the emergency contact.

The wearable alert system 300 may provide functionality for a user to store the contact information of an emergency contact in the user profile associated with the user and the wearable alert device 100. In order to prevent the wearable alert device 100 from outputting a false alarm, the wearable alert device 100 may first output an alert to the user of the device 100 that the system 300 has determined that the user may be experiencing an abnormal physiological condition and provide functionality for the user to indicate via an input device that the user does not wish to output an alert to the emergency contact. The wearable alert system 300 may output an alert indicating that the user of the wearable alert device 100 may be experiencing an abnormal physiological condition and the real-time location of the wearable alert device 100 stored in the device location database 340.

Figure 4:
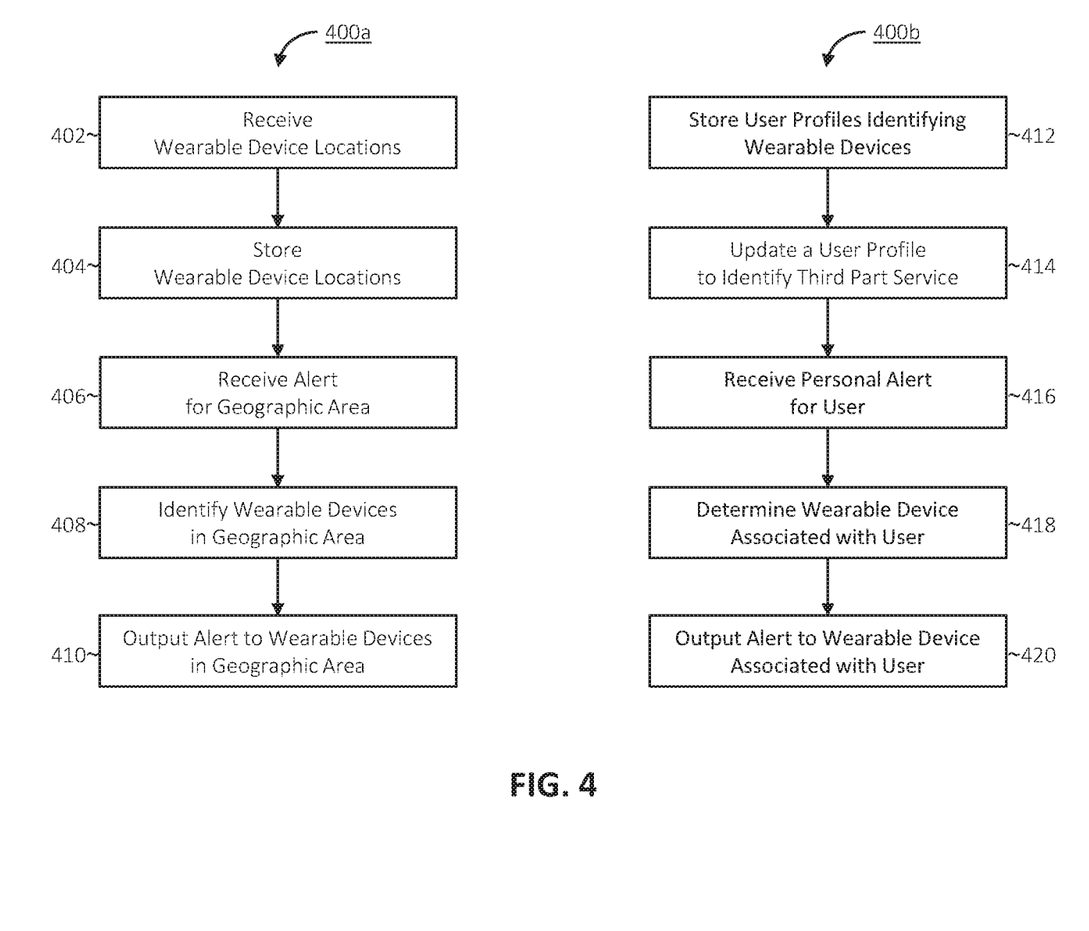
FIG. 4 are flowcharts that illustrates processes for outputting alerts according to exemplary embodiments of the present invention.

FIG. 4 are flowcharts that illustrates a process 400a and a process 400b for outputting alerts according to exemplary embodiments of the present invention. The wearable alert system 300 may perform either or both of the processes 400a and 400b separately or in combination.

Referring to the process 400a, the wearable alert system 300 receives information indicative of real-time locations of wearable alert devices 100 in step 402. A real-time location of a wearable alert device 100 may be determined by the wearable alert device 100 and/or by the server 210 or other network device. Additionally or alternatively, the wearable alert device 100 may be paired with a portable electronic device (e.g., a smartphone, a vehicle, etc.) and the real-time location of the wearable alert device 100 may be determined based on a location of the portable electronic device.

The wearable alert system 300 stores information indicative of the real-time locations of wearable alert devices 100 in the device location database 340 in step 404. The wearable alert system 300 may repeatedly receive information indicative of real-time locations of wearable alert devices 100 and may automatically and repeatedly update the device location database 340 to reflect the real-time locations of the wearable alert devices 100.

The wearable alert system 300 receives information indicative of a potentially dangerous condition in a geographic area in step 406. The information indicative of a potentially dangerous condition may be, for example, weather alert 322, public safety alert 324, and/or an environmental alert 326 as described above.

The wearable alert system 300 identifies the wearable alert devices 100 that are located in the geographic area in step 408.

The wearable alert system 300 outputs alerts to a communications network 230 for transmittal to the wearable alert devices 100 that are located in the geographic area in step 410.

Referring to the process 400b, the wearable alert system 300 stores user profiles in the user profile database 380 in step 412. Each of the user profiles identifies at least one wearable alert device 100.

The wearable alert system 300 updates a profile to identify one or more third party services (e.g., a vehicle tracking system, a subscription-based vehicle-based alert system, a home security monitoring system, etc.) such that the user may receive personal alerts 328 via the wearable alert system 300 in step 414.

The wearable alert system 300 receives a personal alert 328 for the user in step 416. The personal alert 328 may be received from a third party service identified in step 414.

The wearable alert system 300 determines the at least one wearable alert device 100 associated with the user in step 418.

The wearable alert system 300 outputs an alert to a communications network 230 for transmittal to the at least one wearable alert device 100 associated with the user in step 420.

Figure 5:
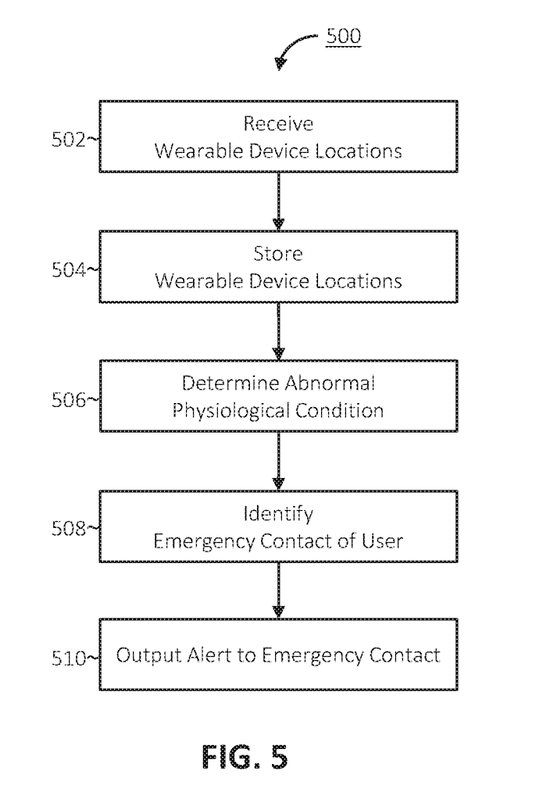
FIG. 5 is a flowchart that illustrates a process for outputting an alert to an emergency contact according to an exemplary embodiment of the present invention.

FIG. 5 is a flowchart that illustrates a process 500 for outputting an alert to an emergency contact according to an exemplary embodiment of the present invention.

The wearable alert system 300 receives information indicative of real-time locations of wearable alert devices 100 in step 502. A real-time location of a wearable alert device 100 may be determined by the wearable alert device 100 and/or by the server 210 or other network device. Additionally or alternatively, the wearable alert device 100 may be paired with a portable electronic device (e.g., a smartphone, a vehicle, etc.) and the real-time location of the wearable alert device 100 may be determined based on a location of the portable electronic device.

The wearable alert system 300 stores information indicative of the real-time locations of wearable alert devices 100 in the device location database 340 in step 504. The wearable alert system 300 may repeatedly receive information indicative of real-time locations of wearable alert devices 100 and may automatically and repeatedly update the device location database 340 to reflect the real-time locations of the wearable alert devices 100.

The wearable alert system 300 determines that a user may be experiencing an abnormal physiological condition (and outputs an indication that the user may be experiencing an abnormal physiological condition, which is received by the analysis unit 360) in step 506. As described above, the wearable alert device 100 and/or the analysis unit 360 may determine the abnormal physiological condition based on the output of one or more physiological sensors 180 and/or position sensors 170.

The wearable alert system 300 determines the emergency contact of the user of the wearable alert device 100 in step 508. The emergency contact may be stored in the user profile associated with the user and the wearable alert device 100.

The wearable alert system 300 outputs an alert to the emergency contact of the user of the wearable alert device 100 in step 510. The alert may include the real-time location of the wearable alert device 100 received in step 502 and stored in the device location database 340 in step 504 and an indication that of the wearable alert device 100 may be experiencing an abnormal physiological condition.

While preferred embodiments have been set forth above, those skilled in the art who have reviewed the present disclosure will readily appreciate that other embodiments can be realized within the scope of the invention. For example, disclosures of specific numbers of hardware components, software modules and the like are illustrative rather than limiting. Therefore, the present invention should be construed as limited only by the appended claims.

What is claimed is:

1. A computer-implemented method, comprising:
storing a user profile associating a wearable alert device with a user by one or more servers that are remote from the wearable alert device, the user profile including contact information for an emergency contact;
repeatedly receiving, by the one or more remote servers, information indicative of a real-time location of the wearable alert device;
automatically and repeatedly updating a remote device location database, by the one or more remote servers, to reflect the real-time location of the wearable alert device;
receiving, from the wearable alert device, information indicating that the user of the wearable alert device is potentially experiencing an abnormal physiological condition; and
outputting an alert including the real-time location of the wearable alert device and an indication that the user of the wearable alert device is potentially experiencing the abnormal physiological condition to a communications network for transmittal to the emergency contact,
wherein, to prevent the output of a false alarm, the user of the wearable alert device is provided with functionality to cancel the alert.

2. The method of claim 1, wherein:
the wearable alert device includes one or more physiological sensors that determine one or more physiological parameters of the user; and
the determination that the user is potentially experiencing the abnormal physiological condition is based on the one or more physiological parameters.

3. The method of claim 2, wherein:
the wearable alert device determines that the user is potentially experiencing the abnormal physiological condition based on the one or more physiological parameters;
the wearable alert device outputs the information indicating that the user is potentially experiencing the abnormal physiological condition to the communications network for transmittal to the one or more remote servers; and
the one or more remote servers output the alert.

4. The method of claim 2, wherein:
the wearable alert device outputs the one or more physiological parameters to the communications network for transmittal to the one or more remote servers;
the one or more remote servers determine that the user is potentially experiencing the abnormal physiological condition based on the one or more physiological parameters; and
the one or more remote servers output the alert.

5. The method of claim 2, wherein the one or more physiological parameters comprise body temperature, heart rate, brain activity, muscle motion, sweat rate, blood pressure, pulse oximetry, blood chemistry, respiratory rate, electrodermal activity, or brain waves.

6. The method of claim 1, wherein:
the wearable alert device includes one or more position sensors that determine a position of the user relative to a ground level; and
the determination that the user is potentially experiencing the abnormal physiological condition is based on the position of the user relative to the ground level.

7. The method of claim 1, wherein the real-time location of the wearable alert device is determined by the wearable alert device.

8. The method of claim 1, wherein the real-time location of the wearable alert device is determined by a network device.

9. The method of claim 1, wherein the wearable alert device wirelessly communicates with a portable electronic device and the real-time location of the wearable alert device is determined based on a location of the portable electronic device.

10. A system, comprising:
a user profile database that stores a user profile associating a wearable alert device with a user, the user profile including contact information for an emergency contact;
a device location database that stores information indicative of a real-time location of the wearable alert device; and
a server, remote from the wearable alert device, that:
repeatedly receives information indicative of the real-time spatial location of the wearable alert device;
automatically and repeatedly updates the device location database;
receives, from the wearable alert device, information indicating that the user of the wearable alert device is potentially experiencing an abnormal physiological condition; and
outputs an alert including the real-time location of the wearable alert device and an indication that the user of the wearable alert device is potentially experiencing the abnormal physiological condition to a communications network for transmittal to the emergency contact,
wherein, to prevent the output of a false alarm, the user of the wearable alert device is provided with functionality to cancel the alert.

11. The system of claim 10, wherein:
the wearable alert device includes one or more physiological sensors that determine one or more physiological parameters of the user; and
the determination that the user is potentially experiencing the abnormal physiological condition is based on the one or more physiological parameters.

12. The system of claim 11, wherein:
the wearable alert device determines that the user is potentially experiencing the abnormal physiological condition based on the one or more physiological parameters; and
the wearable alert device outputs the information indicating that the user is potentially experiencing the abnormal physiological condition to the communications network for transmittal to the server.

13. The system of claim 11, wherein:
the wearable alert device outputs the one or more physiological parameters to the communications network for transmittal to the server; and
the server determines that the user is potentially experiencing the abnormal physiological condition based on the one or more physiological parameters.

14. The system of claim 11, wherein the one or more physiological parameters comprise body temperature, heart rate, brain activity, muscle motion, sweat rate, blood pressure, pulse oximetry, blood chemistry, respiratory rate, electrodermal activity, or brain waves.

15. The system of claim 10, wherein:
the wearable alert device includes one or more position sensors that determine a position of the user relative to a ground level; and
the determination that the user is potentially experiencing the abnormal physiological condition is based on the position of the user relative to the ground level.

16. The system of claim 10, wherein the real-time location of the wearable alert device is determined by the wearable alert device.

17. The system of claim 10, wherein the real-time location of the wearable alert device is determined by a network device.

18. The system of claim 10, wherein the wearable alert device wirelessly communicates with a portable electronic device and the real-time location of the wearable alert device is determined based on a location of the portable electronic device.

* * * * *